(12) United States Patent
Kudo et al.

(10) Patent No.: US 7,078,583 B2
(45) Date of Patent: Jul. 18, 2006

(54) ELONGATED ABSORBENT ARTICLE

(75) Inventors: Jun Kudo, Kagawa (JP); Kenichiro Kuroda, Kagawa (JP); Takuya Miyama, Kagawa (JP); Masataka Kinoshita, Kagawa (JP)

(73) Assignee: Uni-Charm Corporation, Shikokuchuo (JP)

( * ) Notice: Subject to any disclaimer, the term of this patent is extended or adjusted under 35 U.S.C. 154(b) by 0 days.

(21) Appl. No.: 11/038,886

(22) Filed: Jan. 18, 2005

(65) Prior Publication Data

US 2005/0124951 A1 Jun. 9, 2005

Related U.S. Application Data

(63) Continuation of application No. PCT/JP03/15391, filed on Dec. 2, 2003.

(30) Foreign Application Priority Data

Dec. 5, 2002 (JP) ............................. 2002-354178

(51) Int. Cl.
*A61F 13/15* (2006.01)
(52) U.S. Cl. .................. 604/380; 604/378; 604/385.01
(58) Field of Classification Search ................ 604/379, 604/380, 385.01, 385.03, 385.201, 385.23, 604/385.24, 386, 387
See application file for complete search history.

(56) References Cited

U.S. PATENT DOCUMENTS

| 5,171,302 | A | * | 12/1992 | Buell | ..................... | 604/385.23 |
| 5,197,959 | A | * | 3/1993 | Buell | ..................... | 604/385.23 |
| 5,300,055 | A | * | 4/1994 | Buell | ..................... | 604/385.23 |
| 5,591,150 | A | * | 1/1997 | Olsen et al. | ........... | 604/385.23 |
| 5,891,118 | A | * | 4/1999 | Toyoshima et al. | ......... | 604/366 |
| 5,941,861 | A | * | 8/1999 | Ng | ............... | 604/366 |
| 6,159,190 | A | * | 12/2000 | Tanaka et al. | ......... | 604/385.24 |
| 6,326,525 | B1 | * | 12/2001 | Hamajima et al. | .......... | 604/378 |
| 6,371,948 | B1 | * | 4/2002 | Mizutani | ............... | 604/385.01 |
| 6,394,989 | B1 | * | 5/2002 | Mizutani | ............... | 604/385.01 |
| 6,413,248 | B1 | * | 7/2002 | Mizutani | ............... | 604/385.17 |
| 2004/0249355 | A1 | * | 12/2004 | Tanio et al. | ........... | 604/385.01 |
| 2005/0027278 | A1 | * | 2/2005 | Mizutani et al. | ............ | 604/387 |
| 2005/0080391 | A1 | * | 4/2005 | Yoshimasa et al. | .... | 604/385.01 |

(Continued)

FOREIGN PATENT DOCUMENTS

JP 1-147815 10/1989

(Continued)

OTHER PUBLICATIONS

Komatsu, et al., U.S. Appl. No. 10/964,541, "Absorbent Article with Flexible Hinge", Oct. 13, 2004.

*Primary Examiner*—Tatyana Zalukaeva
*Assistant Examiner*—Michael G. Bogart
(74) *Attorney, Agent, or Firm*—Darby & Darby

(57) ABSTRACT

Disclosed is an elongated absorbent article including: rear inner compressed grooves disposed in a rear half of the absorbent article and extending symmetrically about a longitudinal centerline of the absorbent article, defining therebetween a rear central region; and a rear connecting compressed groove connecting rear ends of the rear inner compressed grooves, defining a rear end of the rear central region. A liquid absorbent layer is recessed in the rear central region from the side of the garment surface toward the skin surface to have a backside compressed portion extending along the longitudinal centerline. The backside compressed portion has a rear end positioned forward of the rear connecting compressed groove.

18 Claims, 9 Drawing Sheets

U.S. PATENT DOCUMENTS

2005/0148973 A1 * 7/2005 Tamura et al. ............. 604/380

FOREIGN PATENT DOCUMENTS

| JP | 3-33622 | 4/1991 |
| JP | 10-155832 A1 | 6/1998 |
| JP | 10-328233 A1 | 12/1998 |
| JP | 2001-095842 A1 | 4/2001 |
| WO | WO 2004/049997 A1 * | 12/2003 |

* cited by examiner

ELONGATED ABSORBENT ARTICLE

CROSS-REFERENCE TO RELATED APPLICATIONS

This application is a Continuation of International Application No. PCT/JP03/15391 filed Dec. 2, 2003, which application designated the United States and was published in Japanese on Jun. 17, 2004 as WO 2004/049997 A1 under PCT Article 21(2).

International Application No. PCT/JP03/15391 claims priority under 35 U.S.C. § 119 from Japanese Patent Application JP 2002-354178, which was filed on Dec. 5, 2002.

BACKGROUND OF THE INVENTION

1. Field of the Invention

The present invention relates to an absorbent article suitable for absorbing menstrual blood and so on discharged from a woman's genital organ, more particularly, relates to an elongated absorbent article intended to cover the wearer's body from a vaginal opening to buttocks.

2. Description of the Related Art

Absorbent articles intended to absorb menstrual blood discharged from a woman's genital organ are typically constructed to include a liquid-permeable topsheet appearing on its skin surface, a liquid-impermeable backsheet appearing on its garment surface and a liquid absorbent layer disposed between the topsheet and the backsheet, and generally, they are worn with the backsheet adhered to an inner side of a groin piece of an undergarment through a pressure-sensitive adhesive layer.

In such an absorbent article, the function of certainly collecting menstrual blood applied to the skin surface is required so as to prevent lateral leakage of liquid and rearward leakage of liquid from the absorbent article.

Particularly in an absorbent article that is intended to be worn by a woman during menstruation while sleeping, required is not only prevention of lateral leakage of menstrual blood from the absorbent article but certain absorption of menstrual blood trying to flow along the wearer's body toward the anus and the cleft of the buttocks or trying to flow along the skin surface of the absorbent article rearwardly without causing any leakage. Accordingly, such an absorbent article for nighttime use is elongated more than absorbent articles for daytime use so that its skin surface can cover a large area from a mons pubis which is anterior to the vaginal opening to the buttocks which is posterior to the anus.

In sanitary napkins of this kind, there have been known ones whose skin surface can easily fit in the woman's crotch, wherein compressed grooves are formed in the liquid absorbent layer so as to function as flexible hinges.

Japanese Unexamined Patent Publication No. 10-328233 (Patent Publication 1) discloses an elongated sanitary napkin whose rear portion can cover the buttocks of a wearer. In a front portion of this sanitary napkin, a pair of longitudinally extending topside grooves is formed in the skin surface; in a rear portion thereof, a longitudinally extending rear groove is formed in the garment surface. The topside grooves are spaced longitudinally apart from the rear groove so as not to overlap as viewed from a lateral direction. In this sanitary napkin, since the topside grooves in the front portion can function as flexible hinges, a central portion positioned between the topside grooves can be easily deformed in an arch-like state toward the wearer's body so as to come into close contact with the excretory part, and in addition, since the napkin can be easily deformed in the rear portion to bulge toward the wearer's body along the rear groove, the bulging portion can easily fit in the cleft of the buttocks.

On the other hand, Japanese Unexamined Utility-Model Publication No. 3-33622 (Patent Publication 2) discloses a sanitary napkin, in which a pair of longitudinally extending first compressed grooves is formed in the skin surface of the napkin, while a longitudinally extending second compressed groove is formed in the garment surface of the napkin at an intermediate position between the first compressed grooves in pair. This sanitary napkin can be easily deformed into a W-shaped cross section such that the central portion of the napkin is deformed at the second compressed groove to bulge toward the wearer's skin while both side portions of the napkin are deformed at the first compressed grooves to bulge toward the garment, whereby the central portion of the napkin comes into close contact with the excretory part of the wearer's body.

In the sanitary napkin disclosed in Patent Publication 1, the rear groove is formed in its rear portion so that the portion having the rear groove can fit in the cleft of the buttocks. However, since the rear portion is flat except for the rear groove, if the rear groove is pressed against the cleft of the buttocks, such as by elastic members provided centrally of a back body of sanitary shorts, portions at both sides of the rear groove tend to deform away from the buttocks due to a reaction force to the pressure given to the rear groove. Accordingly, a space is easily left between the surface of the buttocks and the rear portion of the sanitary napkin.

In the sanitary napkin disclosed in Patent Publication 2, on the other hand, the sanitary napkin can be easily deformed into a W-shaped cross section when subjected to a lateral pressure from the thighs, so that the central portion of the skin surface can easily come into close contact with the vaginal opening. However, if the construction disclosed in Patent Publication 2 is adopted for a rear portion of a sanitary napkin that is intended to contact the buttocks, the rear portion of the sanitary napkin cannot closely conform to the curved surface of the buttocks. More specifically, since the buttocks have a cleft posterior to the anus and are three-dimensionally outwardly curved at both sides of the cleft, the rear portion of the sanitary napkin that is deformed in a W-shaped cross section hardly conforms to the three-dimensionally outwardly curved surface. Therefore, leaving a space between the surface of the buttocks and the rear portion of the sanitary napkin cannot be prevented.

SUMMARY OF THE INVENTION

The present invention has been worked out in view of the shortcomings in the prior art set forth above. It is therefore an object of the present invention to provide an absorbent article whose rear portion can easily fit in the cleft of the buttocks and can be easily deformed in portions other than the portion intended to fit in the cleft to have a three-dimensionally concavely curved surface in accordance with the contour of the buttocks.

According to the present invention, there is provided an elongated absorbent article comprising: a liquid-permeable topsheet appearing on a skin surface; a backsheet appearing on a garment surface; and a liquid absorbent layer disposed between the topsheet and the backsheet, the absorbent article having compressed groove where the skin surface is recessed toward the garment surface with the liquid absorbent layer compressed together with the topsheet, wherein the compressed groove includes: rear inner compressed grooves disposed in a rear half of the absorbent article and extending symmetrically about a longitudinal centerline of the absorbent article, defining therebetween a rear central region; and a rear connecting compressed groove connecting rear ends of the rear inner compressed grooves, defining a rear end of the rear central region, wherein the liquid absorbent layer is recessed in the rear central region from the side of the garment surface toward the skin surface to have a backside compressed portion extending along the longitudinal centerline, the backside compressed portion having a rear end positioned forward of the rear connecting compressed groove.

In this absorbent article, when the rear central region is pressed against the cleft of the buttocks by a tightening force of an undergarment, the rear central region having the backside compressed portion can be deformed to fit in the cleft of the buttocks. Since the rear central region having the backside compressed portion is surrounded by the rear inner compressed grooves and the rear connecting compressed groove, portions outside the rear central region that is deformed to bulge toward the cleft of the buttocks can be easily curved concavely three-dimensionally with starting point at the rear inner compressed grooves and the rear connecting compressed groove. Thus, while the rear central region can enter the cleft of the buttocks, the surrounding portions can conform to the curved surface of the buttocks, thereby improving contact between the buttocks and the absorbent article.

In the present invention, the rear inner compressed grooves may be formed to gradually decrease a separation distance therebetween rearwardly of the absorbent article.

With this construction, the rear central region can easily enter the cleft of the buttocks.

In the present invention, rear outer compressed grooves may be disposed laterally outside the rear inner compressed grooves to extend longitudinally of the absorbent article.

With this construction, portions outside the rear central region can be easily curved concavely three-dimensionally.

Preferably, the rear outer compressed grooves are connected with each other at a position spaced rearwardly apart from the rear connecting compressed groove.

With this construction, since the compressed grooves are doubled in a rear portion of the absorbent article, the absorbent article can be easily curved concavely three-dimensionally in the rear portion.

In the present invention, density of the liquid absorbent layer may be higher in regions positioned between the rear inner compressed grooves and the rear outer compressed grooves than in the rear central region.

With the density of the liquid absorbent layer thus increased outside the rear inner compressed grooves, the portions outside the rear central region can be kept in a three-dimensionally concavely curved state, preventing occurrence of distortion or twist due to a pressure from the wearer's body.

The present invention may also be constructed such that the compressed groove further includes: front inner compressed grooves extending forwardly from the rear inner compressed grooves without interruption; and front outer compressed grooves disposed laterally outside the front inner compressed grooves to extend longitudinally of the absorbent article, wherein inflected portions are provided at boundaries between the rear inner compressed grooves and the front inner compressed grooves to increase a separation distance between laterally opposed compressed grooves, the rear outer compressed grooves being spaced apart from the front outer compressed grooves in portions laterally outside the inflected portions.

In the absorbent article thus constructed, the widened portion positioned between the inflected portions intensively receives a pressure from four directions due to the presence of the front outer compressed grooves and the rear outer compressed grooves positioned forward and rearward thereof, the widened portion positioned between the inflected portions can be bulged toward the perineum of a wearer to come into close contact with the perineum. Leakage of menstrual blood from the rear end of the absorbent article toward the buttocks can be effectively prevented by such close contact with the perineum, the fit of the rear central region into the cleft of the buttocks, and the deformation into a three-dimensionally concavely curved state.

In the present invention, elastically extensible members for exerting an elastic shrinkage force on the skin surface in the longitudinal direction may be disposed so that rear action ends of the elastically extensible members are positioned forward of or in the vicinities of front ends of the rear outer compressed grooves.

Since front and rear portions of the absorbent article are attracted to each other with such elastically extensible members, the absorbent article can be easily recessed to conform to the contour of the wearer's body. Here, since the rear outer compressed grooves are positioned rearward of the action ends of the elastically extensible members, the elastic shrinkage force of the elastically extensible members does not act on the rear inner compressed grooves and the rear outer compressed grooves disposed around the rear central region, so that the portions outside the rear central region can be certainly kept in a concavely curved state.

In the present invention, it is also preferred that the backsheet is bonded to the backside compressed portion of the liquid absorbent layer so that the backsheet fits in the recess of the backside compressed portion.

With the backsheet fitting in the recess of the backside compressed portion, the material of the backsheet functions to reinforce the shape of the backside compressed portion, so that the liquid absorbent layer can be certainly maintained in a bulging state along the backside compressed portion.

Also preferably, a pressure-sensitive adhesive layer is disposed on an exterior surface of the backsheet in a region elongated longitudinally of the absorbent article to cover the backside compressed portion.

With this construction, since the backsheet can be firmly fixed to an undergarment within the elongated region covering the backside compressed portion, the backside compressed portion can be prevented from being displaced from the center of the undergarment, so that the portion including the backside compressed portion can be certainly pressed into the cleft of the buttocks by a tightening force of the undergarment.

BRIEF DESCRIPTION OF THE DRAWINGS

The present invention will be understood more fully from the detailed description given hereinafter and from the accompanying drawings of the preferred embodiments of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

In the present invention, the absorbent article refers to a sanitary napkin whose primary object is to absorb menstrual blood discharged from the vaginal opening of a woman. It should be noted that the absorbent article has two major surfaces: of which one surface intended to be worn toward the wearer's crotch is referred to as "skin surface", while the other surface is referred to as "garment surface" regardless of whether a garment is worn outside the absorbent article or not.

As used herein, the term "longitudinal centerline" refers to a line which extends longitudinally to divide the absorbent article laterally in two. On the other hand, the term "lateral reference line" does not necessarily refer to a line which extends laterally to divide the absorbent article longitudinally in two, but refers to a line which extends laterally to cross a longitudinal center of a portion intended to be brought into contact with the vaginal opening during wear.

The compressed grooves and the backside compressed portion may be formed such that a recess is extended in the shape of a continuous line or such that discrete compressed portions are arranged in a row. The rear central region refers to a region that is intended to face a portion of a wearer's body positioned posterior to the vaginal opening and including the anus and the cleft of the buttocks, while a front central region refers to a region that is intended to contact the vaginal opening. The boundary between the front central region and the rear central region is intended to face the perineum positioned between the vaginal opening and the anus.

Figure 1:
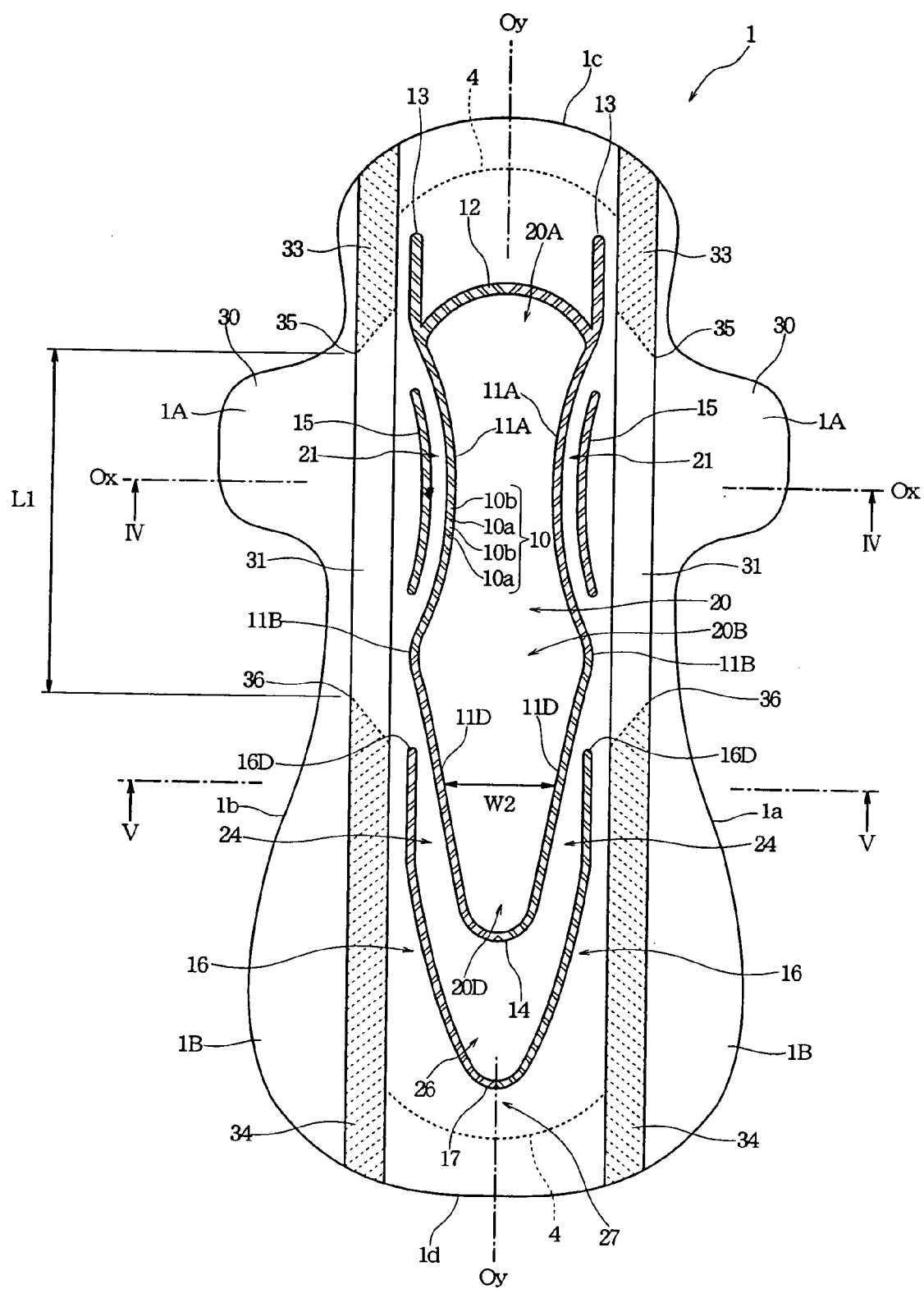
FIG. 1 is a top plan view showing a sanitary napkin as an absorbent article according to one embodiment of the present invention, in which a pattern of compressed groove is mainly shown.
Figure 2:
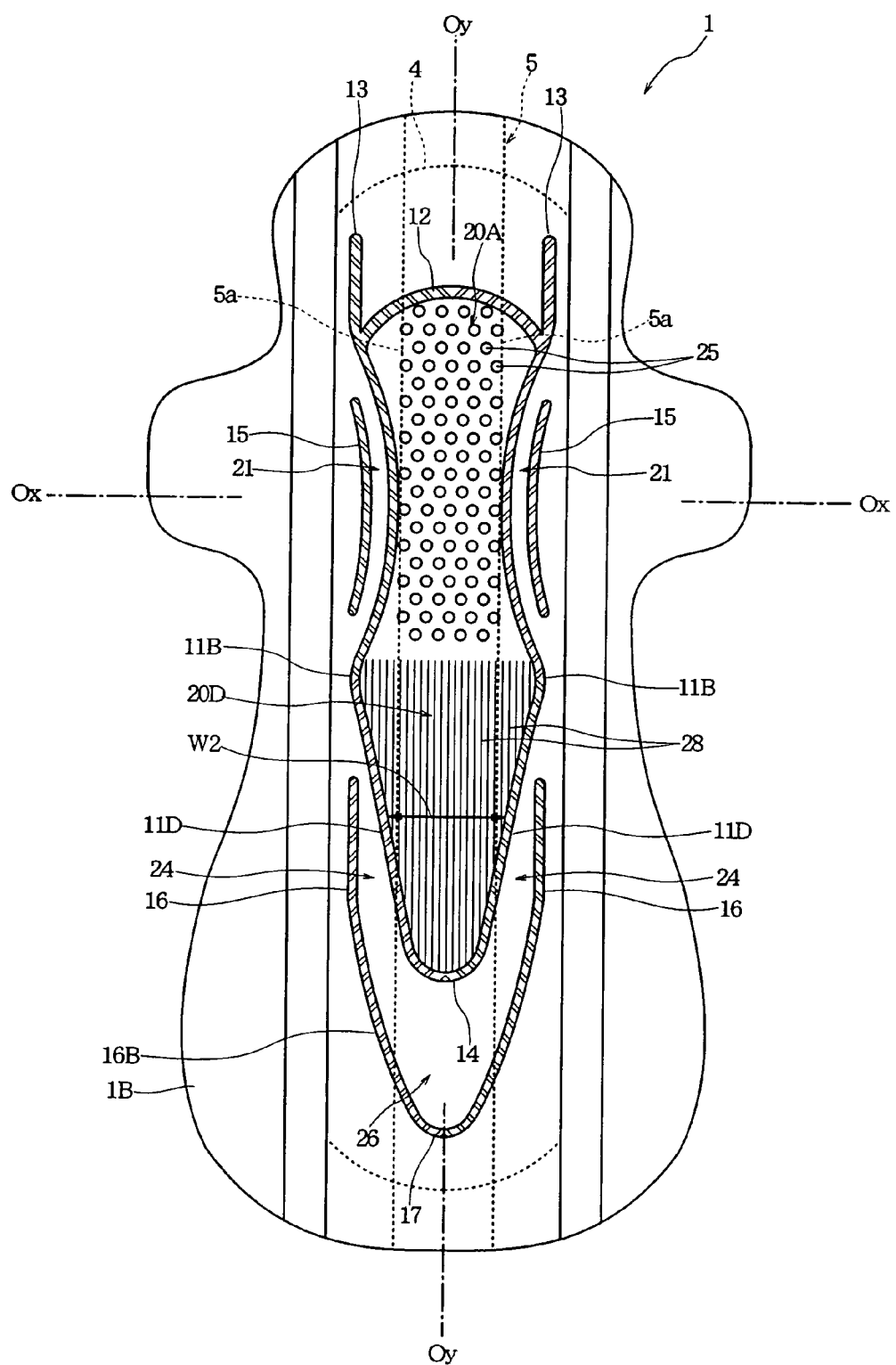
FIG. 2 is a top plan view showing a sanitary napkin as an absorbent article according to one embodiment of the present invention, in which a configuration of a topsheet is mainly shown.
Figure 3:
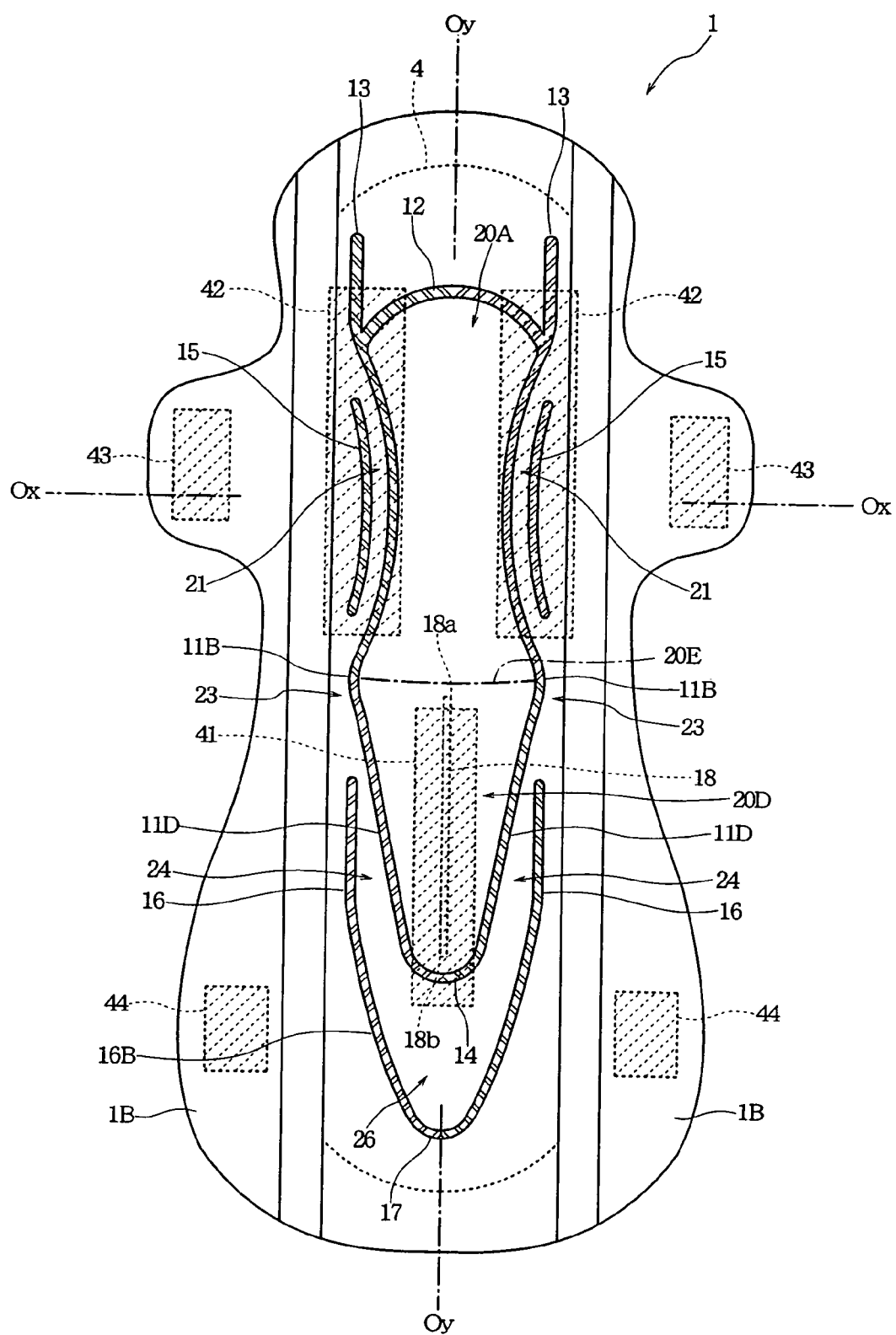
FIG. 3 is a top plan view showing a sanitary napkin as an absorbent article according to one embodiment of the present invention, in which a backside compressed portion and an arrangement of pressure-sensitive adhesive layers are mainly shown.

FIGS. 1 to 3 are top plan views showing a sanitary napkin 1 as an absorbent article according to one embodiment of the present invention, wherein the skin surface faces upward. Although showing the same sanitary napkin 1, FIGS. 1 to 3 are prepared as different drawings for convenience of explanation of individual components. FIG. 1 mainly shows a pattern of compressed groove, FIG. 2 shows a configuration of a topsheet, and FIG. 3 shows a backside compressed portion and an arrangement of pressure-sensitive adhesive layers.

Figure 4:
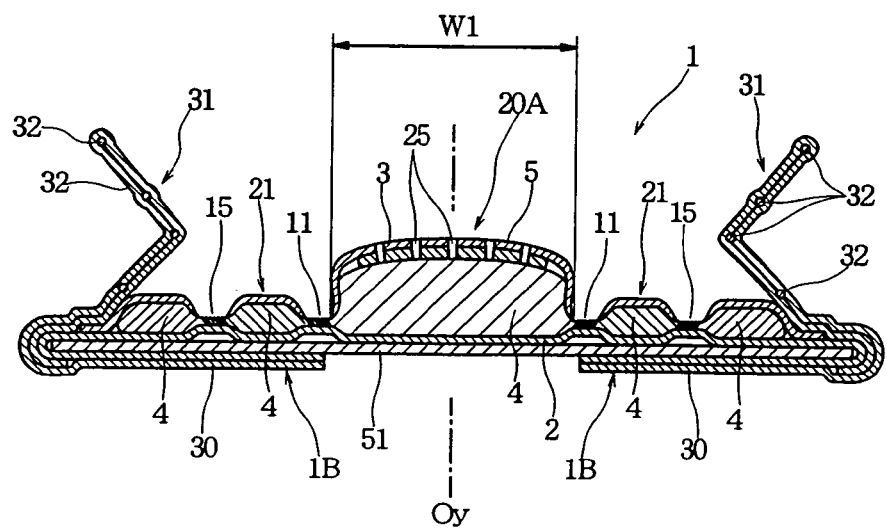
FIG. 4 is a sectional view taken along line IV—IV, in which the sanitary napkin is attached to a groin piece.
Figure 5:
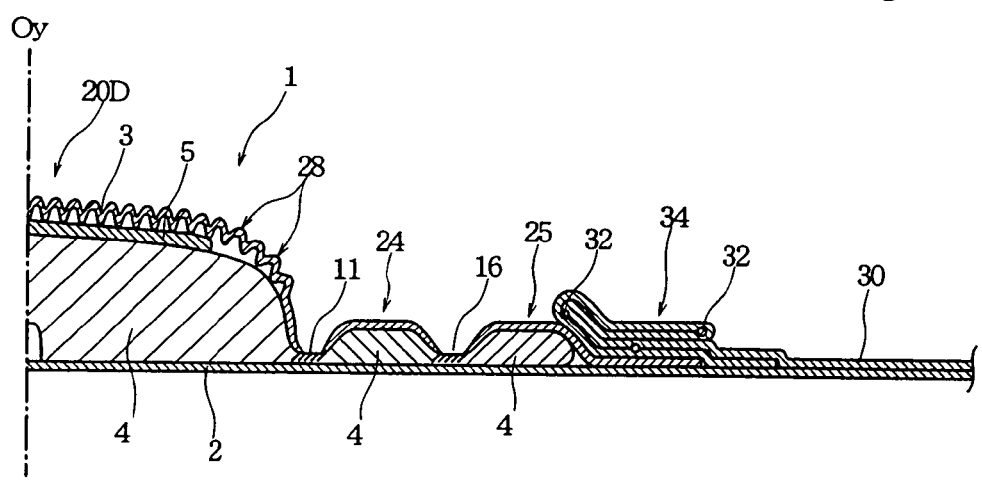
FIG. 5 is a half sectional view of the sanitary napkin taken along line V—V of FIG. 1.

FIG. 4 is a sectional view taken along line IV—IV (lateral reference line), in which the sanitary napkin 1 is attached to a groin piece of an undergarment, and FIG. 5 is a half sectional view taken along line V—V, showing a rear portion of the sanitary napkin 1.

The sanitary napkin 1 of FIGS. 1 to 3 is an elongated sanitary napkin that is suitable for nighttime use by a woman during menstruation, wherein the entire length in the longitudinal direction is from about 200 to 450 mm.

The sanitary napkin 1 has longitudinally extending right and left side edges 1a and 1b that are laterally spaced an equal distance apart from a longitudinal centerline Oy—Oy and outwardly curved front and rear end edges 1c and 1d that are longitudinally spaced apart from a lateral reference line Ox—Ox. The distance from the lateral reference line Ox—Ox to the rear end edge 1d is larger than the distance from the lateral reference line Ox—Ox to the front end edge 1c.

Within a range having a given length in the longitudinal direction and containing the lateral reference line Ox—Ox, the right and left side edges 1a and 1b project laterally outwardly, thereby providing wings 1A and 1A. Rearward of the wings 1A and 1A, furthermore, the right and left side edges 1a and 1b are curved to gradually rearwardly increase the lateral separation distance therebetween, thereby providing rear flaps 1B and 1B.

As shown in the sectional view of FIG. 4, the sanitary napkin 1 comprises a liquid-impermeable backsheet 2 appearing on the garment surface and a liquid-permeable topsheet 3 appearing on the skin surface. A liquid absorbent layer 4 is disposed between the backsheet 2 and the topsheet 3, and a second layer 5 is disposed between the topsheet 3 and the liquid absorbent layer 4. As indicated by a dotted line in FIG. 1, the liquid absorbent layer 4 extends over a large area from a position just inside the front end edge 1c to a position just inside the rear end edge 1d, but for the wings 1A, 1A and the rear flaps 1B, 1B.

In the sanitary napkin 1, compressed groove 10 is formed in the skin surface by locally pressing and heating at least the topsheet 3 and the liquid absorbent layer 4. More specifically, the compressed groove 10 is formed by embossing with a heating roller. The compressed groove 10 may be formed such that after the liquid absorbent layer 4 is stacked on the topsheet 3, a smooth surface roller is applied to an exterior surface of the liquid absorbent layer 4 while a heating roller with projections arranged in a pattern for embossing is applied to a surface of the topsheet 3 for pressing and heating.

The compressed groove 10 has high-density compressed portions 10a, in which the liquid absorbent layer 4 and the topsheet 3 are pressed until they get almost filmy, and medium-density compressed portions 10b, in which although doesn't get filmy, the liquid absorbent layer 4 is of a higher density than in portions other than the compressed groove 10. The high-density compressed portions 10a and the medium-density compressed portions 10b alternate with each other to provide continuously recessed grooves where the skin surface of the sanitary napkin 1 is recessed toward the side of the backsheet 2.

As shown in FIG. 1, the compressed groove 10 has several distinct compressed grooves indicated by numerals 11–17.

Longitudinally extending front inner compressed grooves 11A and 11A are disposed symmetrically about the longitudinal centerline Oy—Oy. The front inner compressed grooves 11A and 11A are curved toward the longitudinal centerline Oy—Oy so that separation distance therebetween is minimum at the lateral reference line Ox—Ox. As the front inner compressed grooves 11A and 11A extend rearwardly (toward the rear end edge 1d) from the lateral reference line Ox—Ox, the separation distance therebetween gradually increases. Rearward of the front inner compressed grooves 11A and 11A, on the other hand, there are disposed rear inner compressed grooves 11D and 11D whose separation distance gradually decreases rearwardly. The front inner compressed grooves 11A and 11A are connected to the rear inner compressed grooves 11D and 11D through inflected portions 11B and 11B that are also compressed grooves. The separation distance between the inflected portions 11B and 11B becomes larger than those between the compressed grooves positioned forward and rearward thereof.

Front ends of the front inner compressed grooves 11A and 11A are connected to each other through a front connecting compressed groove 12. The front connecting compressed groove 12 is curved toward the front end edge 1c. From boundaries between the front inner compressed grooves 11A and 11A and the front connecting compressed groove 12, extension compressed grooves 13 and 13 are further extended toward the front end edge 1c. The extension compressed grooves 13 and 13 are disposed symmetrically about the longitudinal centerline Oy—Oy.

Rear ends of the rear inner compressed grooves 11D and 11D are connected to each other through a rear connecting compressed groove 14. The rear connecting compressed groove 14 is curved toward the rear end edge 1d.

Thus, the front inner compressed grooves 11A and 11A, the inflected portions 11B and 11B, the rear inner compressed grooves 11D and 11D, the front connecting compressed groove 12, the extension compressed grooves 13 and 13 and the rear connecting compressed groove 14 are mutually connected. In addition, a given area of the skin surface of the sanitary napkin 1 is surrounded by the front inner compressed grooves 11A and 11A, the rear inner compressed grooves 11D and 11D, the front connecting compressed groove 12 and the rear connecting compressed groove 14, and this surrounded area is referred to as central region 20. The central region 20 is of an elongated shape symmetrical about the longitudinal centerline Oy—Oy, wherein a portion forward of the lateral reference line Ox—Ox is shorter than a portion rearward of the lateral reference line Ox—Ox.

Figure 8:
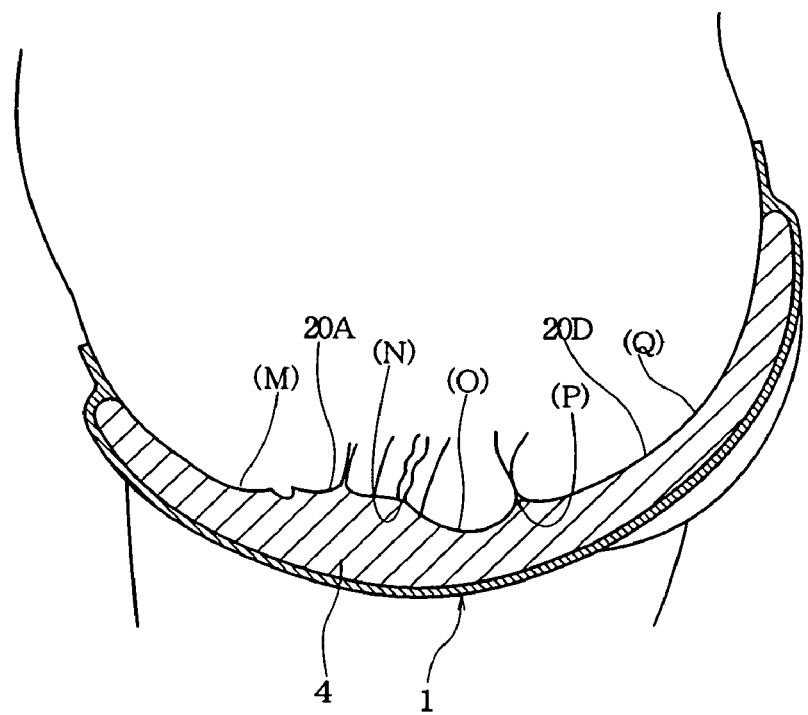
FIG. 8 is an explanatory sectional view showing a state where the sanitary napkin is applied to the woman's crotch.

The central region 20 includes a front central region 20A and a rear central region 20D. FIG. 8 shows a state where the sanitary napkin 1 is applied to the woman's crotch, wherein the front central region 20A is in contact with the vaginal opening (N), while the rear central region 20D is in contact with a portion including the anus (P) and the cleft (Q) of the buttocks. It should be noted that the central region 20 is widened at a portion between the inflected portions 11B and 11B.

In the embodiment shown in FIGS. 1 to 3, the front central region 20A is positioned forward of a straight line 20E connecting the inflected portions 11B and 11B and the rear central region 20D is positioned rearward of the straight line 20E. It should be noted that the widened portion between the inflected portions 11B and 11B is indicated by 20B and the widened portion 20B overlaps with both the front central region 20A and the rear central region 20D.

Laterally outside the front inner compressed grooves 11A and 11A, there are disposed front outer compressed grooves 15 and 15. The front outer compressed grooves 15 and 15 are within a range having a given length forwardly and rearwardly from the lateral reference line Ox—Ox. The front outer compressed grooves 15 and 15 are curved similarly to the front inner compressed grooves 11A and 11A.

Laterally outside the rear inner compressed grooves 11D and 11D, there are disposed rear outer compressed grooves 16 and 16. The rear outer compressed grooves 16 and 16 are inclined to gradually decrease separation distance therebetween toward the rear end edge 1d, and the right and left rear outer compressed grooves 16 and 16 are connected to each other through an outer rear connecting compressed groove 17. The rear outer compressed grooves 16 and 16 and the outer rear connecting compressed groove 17 are continuously formed, wherein the outer rear connecting compressed groove 17 is curved toward the rear end edge 1d.

Laterally outside the widened portion 20B defined between the inflected portions 11B and 11B, the rear ends of the front outer compressed grooves 15, 15 are separated from the front ends 16D, 16D of the rear outer compressed grooves 16, 16. Laterally outside the inflected portions 11B and 11B, therefore, there are provided regions where both the front outer compressed grooves 15, 15 and the rear outer compressed grooves 16, 16 are absent. The distance between the rear ends of the front outer compressed grooves 15, 15 and the front ends 16D, 16D of the rear outer compressed grooves 16, 16 in the longitudinal direction is about 20 to 60 mm.

Figure 7:
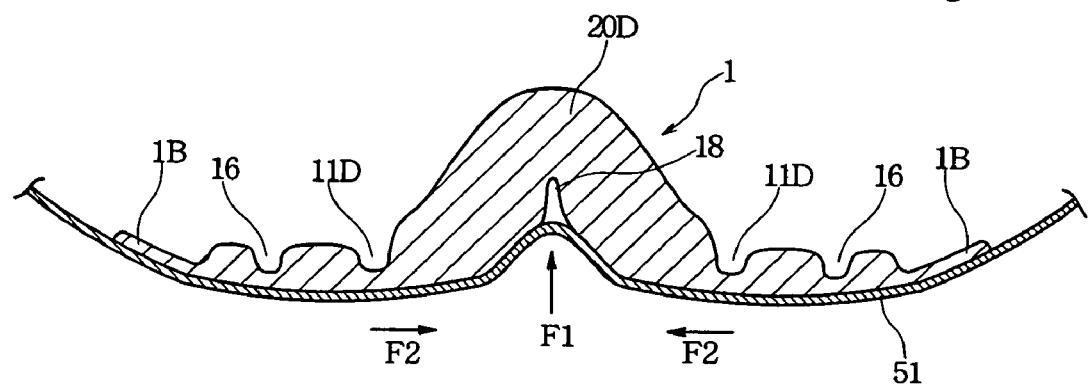
FIG. 7 is a sectional view of the sanitary napkin taken along line VII—VII of FIG. 6.

In the rear central region 20D, as shown in FIGS. 3, 5 and 7, the liquid absorbent layer 4 is recessed from the side of the garment surface toward the skin surface to have a backside compressed portion 18. The backside compressed portion 18 is formed by compressing the liquid absorbent layer 4 from the side of the garment surface and extended along the longitudinal centerline Oy—Oy. The backside compressed portion 18 may be a linear groove, or a row of dot-like compressed portions intermittently arranged in the longitudinal direction, or a row of short linear compressed portions intermittently arranged in the longitudinal direction. As shown in FIG. 3, the backside compressed portion 18 has a front end 18a that is positioned rearward of the straight line 20E and a rear end 18b that is positioned forward of the rear connecting compressed groove 14.

Along the backside compressed portion 18, the liquid absorbent layer 4 is bonded and fixed to the backsheet 2 through a hot-melt adhesive or the like. Alternatively, the liquid absorbent layer 4 may be thermally bonded to the backsheet 2. Thus, the backsheet 2 fits in the recess of the backside compressed portion 18.

As shown in FIG. 2, the second layer 5 is given the shape of a strip elongated to traverse the central region 20 in the longitudinal direction, wherein right and left side edges 5a, 5a are spaced inwardly apart from the front inner compressed grooves 11A, 11A and the rear inner compressed grooves 11D, 11D. Here, the front end of the second layer 5 reaches the front end edge 1c of the sanitary napkin 1, while the rear end reached the rear end edge 1d. Accordingly, the topsheet 3, the second layer 5 and the liquid absorbent layer 4 are compressed together at the front connecting compressed groove 12, the rear connecting compressed groove 14 and the outer rear connecting compressed groove 17. At least in the front central region 20A of the central region and between the second layer 5 and the liquid absorbent layer 4, moreover, there may be provided a liquid acquisition layer, that is formed of a water absorbent sheet such as air-laid nonwoven fabric (air-laid pulp) obtained by bonding hydrophilic fibers such as pulp and synthetic fibers together with a binder into the form of a sheet.

In the front central region 20A, there are regularly arranged a large number of liquid passage holes 25. The liquid passage holes 25 are circular, but may be otherwise shaped, such as elliptical or slit-shaped. Each liquid passage hole 25 has an opening area of 0.2 to 8 $mm^2$, and in case of circle, it has a diameter of 0.5 to 3.2 mm. The center-to-center distance between adjacent liquid passage holes 25 is 1.5 to 8 mm. The liquid passage holes 25 are formed to pass through the topsheet 3 and reach the second layer 5, and preferably, the liquid passage holes 25 are formed to pass through both the topsheet 3 and the second layer 5, as shown in FIG. 4. The liquid passage holes 25 are evenly distributed over the front central region 20A positioned between the straight line 20E connecting the inflected portions 11B, 11B and the front connecting compressed groove 12.

In the rear central region 20D, as shown in FIGS. 2 and 5, the topsheet 3 is shaped to have a corrugated portion 28. Within the corrugated portion 28, more specifically, the topsheet 3 is given a wavy cross-section so that ribs and grooves extend parallel with the longitudinal direction of the article and alternate with each other in the lateral direction of the article. The corrugated portion 28 covers the entire rear central region 20D that is surrounded by the rear inner compressed grooves 11D, 11D, the straight line 20E and the rear connecting compressed groove 14.

Since the topsheet 3 thus provided with the corrugated portion 28 is extensible in the lateral direction, when the rear central region 20D is deformed to bulge toward the wearer's body as shown in FIG. 7, the topsheet 3 is allowed to freely extend in the lateral direction.

The topsheet 3 comprises heat-fusible, thermoplastic fibers, and the second layer 5 also comprises heat-fusible, thermoplastic fibers. Here, the topsheet 3 and the second layer 5 should not be construed as limited to a sheet/layer formed only of such thermoplastic fibers, but may contain other fibers that are not heat-fusible, such as natural fibers and regenerated cellulose fibers, in addition to the thermoplastic fibers.

The liquid passage holes 25 can be formed using heated needles or pins. More specifically, the liquid passage holes 25 can be formed in such a way that after the topsheet 3 and the second layer 5 are stacked, the needles or pins are inserted in a direction from the topsheet 3 to the second layer 5 and then drawn out. At this time, the thermoplastic fibers contained in the topsheet 3 and the thermoplastic fibers contained in the second layer 5 are fusion-bonded together along inner surfaces of the liquid passage holes 25 and therearound. This results in that the opening shape of the liquid passage hole 25 becomes stable and that the portion around the opening of the liquid passage hole 25 is reinforced with the second layer 5. In addition, since the topsheet 3 and the second layer 5 are thermally fusion-bonded together, there is no need for bonding the topsheet 3 and the second layer 5 together through an adhesive, precluding the possibility that the adhesive will interfere with liquid permeation.

The corrugated portion 28 is formed by heat-embossing only the topsheet 3, for example, such that an embossing roller having ribs of a height of 1.8 mm arranged at a pitch of 1.8 mm and another embossing roller having grooves in which the ribs are to be mated are heated to 100 to 125 degrees centigrade and then the topsheet 3 is held between these rollers to form ribs and grooves. Since the topsheet 3 comprises the thermoplastic fibers, it tends to maintain such a corrugated configuration when no external force is exerted thereon, which makes the topsheet 3 extensible in the lateral direction.

The topsheet 3 may be through-air bonded nonwoven fabric. For the through-air bonded nonwoven fabric, sheath/core bicomponent synthetic fibers, of which the core component is polyethylene terephthalate (PET) containing titanium oxide and the sheath component is polyethylene (PE), are bonded together by means of hot air to have a basis weight of about 15 to 60 $g/m^2$. It should be noted that some of the bicomponent synthetic fibers used for the topsheet 3 are coated with a hydrophilic lubricant while the rest are coated with a water-repellent lubricant and they are blended with each other, wherein the blending ratio of the fibers coated with the water-repellent lubricant is preferably 10 to 30% by weight. With the fibers coated with the water-repellent lubricant uniformly contained in the topsheet 3 to have a blending ratio within the above-mentioned range, menstrual blood given to the topsheet 3 can be prevented from being excessively diffused in the topsheet 3, so that menstrual blood can be introduced into the liquid absorbent layer 4 mainly through the liquid passage holes 25.

It should be noted that also in regions other than the liquid passage holes 25, menstrual blood can permeate through the topsheet 3 into the second layer 5. In order to provide the topsheet 3 with such permeability to liquid, the density is preferably equal to or less than 0.12 $g/cm^3$, wherein the lower limit is about 0.025 $g/cm^3$.

The second layer 5 may be through-air bonded nonwoven fabric comprising eccentric sheath/core bicomponent synthetic fibers, of which the core component is polypropylene (PP) and the sheath component is polyethylene (PE). In the through-air bonded nonwoven fabric for the second layer 5, all the fibers are coated with a hydrophilic lubricant. That is, fibers coated with a water-repellent lubricant are not contained. In the present embodiment, the second layer 5 is formed by stacking a plurality of layers of the through-air bonded nonwoven fabric, such as by folding a single through-air bonded nonwoven fabric in three-ply construction. The single through-air bonded nonwoven fabric has a basis weight of about 15 to 50 $g/m^2$, so that the second layer 5 has a basis weight of about 35 to 150 $g/m^2$, preferably 50 to 100 $g/m^2$.

With the basis weight of the second layer 5 made higher than the basis weight of the topsheet 3, the topsheet 3 of a low basis weight and a low density can be reinforced, thereby preventing occurrence of extremely large wrinkles in the topsheet 3 and occurrence of breakage from the liquid passage holes 25.

For example, the topsheet 3 may comprise fibers having a fineness of 2.2 dtex and the second layer 5 may comprise fibers having a fineness of 4.4 dtex so that the fiber density of the second layer 5 is lower than the fiber density of the topsheet 3. The fiber density of the second layer 5 is 0.08 to 0.016 g/cm$^3$.

If the second layer 5 is formed of fibers with high fineness, the second layer 5 can be provided with a three-dimensional fiber network structure to leave a great number of large voids therein. Accordingly, menstrual blood having passed through the topsheet 3 can also pass through the voids under gravitation, so that a large amount of menstrual blood given to the napkin at a time can be rapidly introduced into the liquid absorbent layer 4.

Alternatively, the topsheet 3 and the second layer 5 may be nonwoven fabric other than the through-air bonded nonwoven fabric. For example, the topsheet 3 may be spunlaced nonwoven fabric comprising regenerated cellulose fibers, heat-fusible thermoplastic fibers and optionally also pulp; the second layer 5 may be air-laid nonwoven fabric (air-laid pulp), in which pulp and thermoplastic fibers are accumulated in air, bonded together with a binder, and pressed between heating rollers.

The liquid absorbent layer 4 may be formed by adding synthetic absorbent polymer such as polyacrylate, polyacrylamide and maleic anhydride or natural absorbent polymer such as starch and cellulose to an aggregate of pulp such as ground pulp, mercerized pulp or crosslinked pulp, wherein the pulp and the synthetic absorbent polymer or the like are wrapped in hydrophilic tissue paper.

The backsheet 2 is a liquid-impermeable, breathable sheet such as a polyethylene (PE) or polypropylene (PP) film formed with minute pores. The minute pores may be appropriately distributed over the film for improving breathability such as by adding inorganic filler such as $CaCO_3$ and $BaSO_4$ to the plastic sheet, followed by drawing. The film may have a thickness of about 15 to 50 μm.

The second layer 5 and the liquid absorbent layer 4 are bonded together through a hot-melt adhesive that is partially applied so as not to interfere with liquid permeation. The liquid absorbent layer 4 and the backsheet 2 are also bonded together through a hot-melt adhesive. Therefore, the backsheet 2 can enter the recess of the backside compressed portion 18, as set forth above.

In a manufacturing process of the sanitary napkin 1, after the topsheet 3 in which the corrugated portion 28 has been already formed and the second layer 5 are stacked, the liquid passage holes 25 are formed therein, and then, the liquid absorbent layer 4 and the second layer 5 are bonded together, followed by forming the compressed groove 10 and the backside compressed portion 18. Subsequently, the backsheet 2 is bonded to a surface of the liquid absorbent layer 4. Here, it is also possible to thermally fusion-bond the liquid absorbent layer 4 to the backsheet 2 in such a manner that after the backsheet 2 is thus bonded to the surface of the liquid absorbent layer 4, the backsheet 2 and the liquid absorbent layer 4 are heated together under pressure at the backside compressed portion 18.

The basis weight of the liquid absorbent layer 4 becomes largest at the central region 20. The basis weight at front side regions 21, 21 located between the front inner compressed grooves 11A, 11A and the front outer compressed grooves 15, 15, the basis weight at rear side regions 24, 24 located between the rear inner compressed grooves 11D, 11D and the rear outer compressed grooves 16, 16 and the basis weight at a rear region 26 located between the rear connecting compressed groove 14 and the outer rear connecting compressed groove 17 are all lower than the basis weight at the central region 20. The basis weight of the liquid absorbent layer 4 at the other portions is equal to or slightly lower than those at the front side regions 21, 21, the rear side regions 24, 24 and the rear region 26.

The basis weight of the liquid absorbent layer 4 at the central region 20 is preferably 400 to 1200 g/m$^2$, more preferably 500 to 1000 g/m$^2$. The basis weight at the front side regions 21, 21, the basis weight at the rear side regions 24, 24 and the basis weight at the rear region 26 are preferably 300 to 900 g/m$^2$, more preferably 350 to 600 g/m$^2$. The basis weight of the liquid absorbent layer 4 at the other portions is preferably 200 to 700 g/m$^2$.

As a result, the thickness is increased in the front central region 20A and the rear central region 20D so that the skin surface bulges toward the wearer's body in these regions, as shown in FIGS. 4 and 5.

The compressed grooves 11–17 are formed at a time by heat-embossing with the heating roller. As the topsheet 3 is pressed together with the liquid absorbent layer 4 at the front inner compressed grooves 11A, 11A and the front outer compressed grooves 15, 15, the density of the liquid absorbent layer 4 increases at the front side regions 21, 21 due to tension given to portions of the topsheet 3 covering the front side regions 21, 21.

If the embossing projections arranged on the surface of the heating roller are adapted to have shallow grooves between projections for forming the front inner compressed grooves 11A, 11A and projections for forming the front outer compressed grooves 15, 15, furthermore, the liquid absorbent layer 4 can be pressed with the shallow grooves at the front side regions 21, 21 as the front inner compressed grooves 11A, 11A and the front outer compressed grooves 15, 15 are formed by pressing. In this case, therefore, the density of the liquid absorbent layer 4 can be increased more at the front side regions 21, 21. Likewise, the density of the liquid absorbent layer 4 can be increased more at the rear side regions 24, 24 between the rear inner compressed grooves 11D, 11D and the rear outer compressed grooves 16, 16. The density can also be increased more at the rear region 26 than at the central region 20.

The density of the liquid absorbent layer 4 at the front side regions 21, 21, the rear side regions 24, 24 and the rear region 26 is preferably in the range of 0.08 to 0.2 g/cm$^3$. On the other hand, the density of the liquid absorbent layer 4 at the central region 20 is preferably in the range of 0.05 to 0.18 g/cm$^3$. The density of the liquid absorbent layer 4 at the other regions is preferably in the range of 0.05 to 0.13 g/cm$^3$. It should be noted that the density of the liquid absorbent layer 4 at the front side regions 21, 21 and the rear side regions 24, 24 is preferably higher than that at the central region 20 by at least 0.01 g/cm$^3$, more preferably, by at least 0.02 g/cm$^3$.

It is preferred that the density of the high-density compressed portions 10a and the density of the medium-density compressed portions 10b fall within the range of 0.4 to 1.5 g/cm$^3$.

The length of the central region 20, i.e., the longitudinal distance between the front connecting compressed groove 12 and the rear connecting compressed groove 14 is about 130 to 350 mm. The width W1 of the front central region 20A on the lateral reference line Ox—Ox shown in FIG. 4 is decided according to the width of the woman's genital organ. Because the crotch width of average women is about 30 mm, the width W1 of the front central region 20A is preferably in the range of 15 to 50 mm, more preferably in the range of 20 to 40 mm. On the other hand, the rear central region 20D is so dimensioned as to easily fit in the cleft (Q) of the buttocks of the woman's body shown in FIG. 8, wherein the length, i.e., the longitudinal distance between the straight line 20E connecting the inflected portions 11B, 11B and the rear connecting compressed groove 14 is about 60 to 150 mm. Here, the distance W2 between the rear inner compressed grooves 11D, 11D at a position where the rear central region 20D is longitudinally divided in two is in the range of 15 to 50 mm.

In regions adjacent the right and left side edges 1a and 1b, in which the liquid absorbent layer 4 does not exist, the backsheet 2 and the topsheet 3 are bonded together, and liquid-impermeable sheets 30 and 30 are laid on and bonded to the topsheet 3 and the backsheet 2 through a hot-melt adhesive, as shown in FIGS. 4 and 5. The wings 1A and 1A and the rear flaps 1B and 1B are mainly composed of the backsheet 2 and the liquid-impermeable sheets 30.

The liquid-impermeable sheets 30 are folded in two with a plurality of elastically extensible members 32 interposed therebetween, wherein the confronting surfaces of the folded liquid-impermeable sheet 30 are bonded to each other. In front fixation regions 33 and 33, the liquid-impermeable sheets 30 thus folded in two are refolded and then bonded and fixed to the skin surface in such a folded state. Also in rear fixation regions 34 and 34, the liquid-impermeable sheets 30 are bonded and fixed to the skin surface in such a folded state. In FIG. 1, the front fixation regions 33 and 33 and the rear fixation regions 34 and 34 are indicated by hatching. The rear fixation region 34 is also shown in the sectional view of FIG. 5.

Between the front fixation regions 33, 33 and the rear fixation regions 34, 34, the liquid-impermeable sheets 30 and 30 are free within a given width, whereby the liquid-impermeable sheets 30 and 30 provide leakage preventing walls 31 and 31. The elastically extensible members 32 exert a longitudinal elastic shrinkage force on the leakage preventing walls 31 and 31. Front action ends 35 of the elastic shrinkage force are rear ends of the front fixation regions 33, while rear action ends 36 of the elastic shrinkage force are front ends of the rear fixation regions 34. The action ends 35 and the action ends 36 are attracted to each other due to the elastic shrinkage force, so that the sanitary napkin 1 is deformed with its skin surface recessed within an area of a distance L1 between the action ends 35 and the action ends 36. As a result, the leakage preventing walls 31 and 31 are raised from the skin surface within the area between the action ends 35 and the action ends 36, as shown in FIG. 4.

As shown in FIG. 1, the front action ends 35 are in the same longitudinal position as the boundaries between the front inner compressed grooves 11A and the front connecting compressed grooves 12 or in the vicinity thereof On the other hand, the rear action ends 36 are positioned in the vicinities of or slightly forward of the front ends 16D of the rear outer compressed grooves 16.

Accordingly, the elastic shrinkage force does not act on a front potion where the extension compressed grooves 13 and 13 are present, and therefore, the front portion can be freely deformed without being affected by the elastic shrinkage force. Similarly, since the elastic shrinkage force does not act on a rear portion where the rear outer compressed grooves 16, 16 and the outer rear connecting compressed groove 17 are present, the rear portion of the sanitary napkin 1 can be easily deformed to provide a three-dimensionally concavely curved surface, as will be described hereinbelow.

On the exterior surface of the backsheet 2, as shown in FIG. 3, pressure-sensitive adhesive layers 41–44 are provided. The pressure-sensitive adhesive layer 41 is disposed in a strip-shaped region elongated longitudinally to cover the backside compressed portion 18. The pressure-sensitive adhesive layers 42, 42 are disposed in the front portion of the sanitary napkin 1 symmetrically about the longitudinal centerline Oy—Oy so that one pressure-sensitive adhesive layer 42 is in a region elongated longitudinally to cover one front inner compressed groove 11A and one front outer compressed groove 15 adjacent thereto and the other pressure-sensitive adhesive layer 42 is in a region elongated longitudinally to cover the other front inner compressed groove 11A and the other front outer compressed groove 15 adjacent thereto. On the other hand, the pressure-sensitive adhesive layers 43, 43 are disposed in the wings 1A, 1A; the pressure-sensitive adhesive layers 44, 44 are disposed in the rear flaps 1B, 1B.

When the sanitary napkin 1 is to be attached to the wearer's body, the pressure-sensitive adhesive layer 41 and the pressure-sensitive adhesive layers 42, 42 provided on the exterior surface of the backsheet 2 are adhered to an inner side of a groin piece 51 shown in FIG. 4, and at this time, the rear flaps 1B, 1B are also adhered to the inner side of the undergarment through the pressure-sensitive adhesive layers 44, 44. On the other hand, the wings 1A, 1A are folded back against an outer side of the undergarment to cover both side edges of the groin piece 51, and adhered to the outer side of the groin piece 51 through the pressure-sensitive adhesive layers 43, 43 provided on the garment surface of the wings 1A, 1A.

When the undergarment is worn with the sanitary napkin 1 attached to the groin piece 51, as shown in FIG. 8, the area from the mons pubis (M) to the cleft (Q) of the buttocks in the woman's crotch can be covered with the skin surface of the sanitary napkin 1.

When thus worn, the thighs exert a compressive force toward the longitudinal centerline Oy—Oy on the front outer compressed grooves 15, 15. The compressive force is transmitted to the front side regions 21, 21 of a high density and a high stiffness via the front outer compressed grooves 15, 15, and further to the front inner compressed grooves 11A, 11A. Since the front outer compressed grooves 15, 15 and the front inner compressed grooves 11A, 11A are located sufficiently below the midpoint of the thickness of the front central region 20A, when the compressive force is exerted, the front outer compressed grooves 15, 15, the front side regions 21, 21 and the front inner compressed grooves 11A, 11A try to get under the front central region 20A, so that the front central region 20A is supported from below and raised up toward the wearer's body into close contact with the vaginal opening (N) by the front side regions 21, 21 of a high stiffness.

The front inner compressed grooves 11A, the front side regions 21 and the front outer compressed grooves 15 arranged at both right and left sides of the article are fixed to the inner side of the groin piece 51 through the underlying pressure-sensitive adhesive layers 42, 42. Since the sanitary napkin 1 is adhered to the groin piece 51 with the separation distances between the front inner compressed grooves 11A, between the front side regions 21 and between the front outer compressed grooves 15 maintained, when a compressive force is exerted on the groin piece 51 by the thighs, the sanitary napkin 1 can be deformed together to follow the deformation of the groin piece 51, without causing displacement of the front inner compressed grooves 11A, the front side regions 21 and the front outer compressed grooves 15 from the groin piece 51. Therefore, the front central region 20A to be deformed to bulge toward the wearer's body can always be positioned centrally of the groin piece 51, so that the front central region 20A can be easily brought into close contact with the vaginal opening (N).

In ordinary sanitary shorts, furthermore, elastically extensible members are provided centrally of a back body to extend along the cleft (Q) of the buttocks, so that when applied to the wearer's body, an elastic shrinkage force of the elastically extensible members acts on the groin piece 51 as a hanging-up force.

In the rear central region 20D, the backside compressed portion 18, in which the garment surface of the liquid absorbent layer 4 is recessed, is formed to extend in the longitudinal direction. When a pressure F1 is applied to push up the backside compressed portion 18 toward the wearer's body due to the elastic shrinkage force, as shown in FIG. 7, the rear central region 20D is deformed to bulge, easily coming into close contact with the anus (P) and fitting in the cleft (Q) of the buttocks.

As shown in FIG. 3, since the pressure-sensitive adhesive layer 41 is disposed beneath the backside compressed portion 18, the portion having the backside compressed portion 18 can be firmly fixed to the undergarment. In addition, since the portion of the backsheet 2 where the pressure-sensitive adhesive layer 41 is disposed is bonded to the backside compressed portion 18 of the liquid absorbent layer 4, the hanging-up force of the undergarment can certainly acts on the backside compressed portion 18 of the liquid absorbent layer 4 through the backsheet 2, so that the portion intended to be deformed to bulge due to the presence of the backside compressed portion 18 can be prevented from being displaced from the center of the undergarment.

Since the backside compressed portion 18 is positioned within the rear central region 20D and forward of the rear connecting compressed groove 14, bulging deformation with the backside compressed portion 18 taken as a flexible hinge occurs only in the rear central region 20D.

Since the rear central region 20D is held between the rear inner compressed grooves 11D, 11D extending rearwardly to gradually decrease the separation distance therebetween and its rear end is closed by the rear connecting compressed groove 14, when the rear central region 20D is deformed to bulge toward the wearer's body, forces F2, F2 act on the rear inner compressed grooves 11D, 11D to approximate them each other. When the portions outside the rear central region 20D in such a state are pressed against the wearer's body by the undergarment, the portions laterally outside the rear central region 20D and the portion behind the rear central region 20D can be easily deformed along a curved surface indicated by curved lines X1 and Y1 of FIG. 6, with the rear inner compressed grooves 11D, 11D and the rear connecting compressed groove 14 taken as flexible hinges.

That is, when the rear central region 20D is deformed to bulge toward the cleft (Q) of the buttocks, the rear inner compressed grooves 11D, 11D and the rear connecting compressed groove 14 functioning as flexible hinges become the lowest parts in the concavely curved skin surface so that the right and left side edges 1a, 1b and the rear end edge id of the sanitary napkin 1 project more toward the wearer's body than the flexible hinges. As a result, the portion extending outwardly from the flexible hinges to the right and left side edges 1a, 1b and the rear end edge 1d can be deformed to provide a three-dimensionally concavely curved surface.

The present embodiment is constructed such that the rear outer compressed grooves 16, 16 extending rearwardly to gradually decrease the separation distance therebetween and the outer rear connecting compressed groove 17 are further provided outside the rear inner compressed grooves 11D, 11D and the rear connecting compressed groove 14, so that the rear central region 20D is surrounded at its right, left and rear sides by doubled compressed grooves. Therefore, the rear inner compressed grooves 11D, 11D and the rear connecting compressed groove 17 function as inner flexible hinges, while the rear outer compressed grooves 16, 16 and the outer rear connecting compressed groove 17 function as outer flexible hinges, whereby the rear portion of the sanitary napkin 1 can be deformed to provide a three-dimensionally concavely curved surface more easily.

In the rear side regions 24, 24 and the rear region 26, furthermore, the density of the liquid absorbent layer 4 is increased more than in the rear central region 20D to increase the stiffness, and the rear central region 20D is surrounded at its right, left and rear sides by these regions of a high stiffness. Therefore, the rear portion of the sanitary napkin 1 can be easily kept in the concavely curved state to thereby prevent the concavely curved rear portion from being twisted or wrinkled. Moreover, since the elastic shrinkage force of the elastically extensible members 32 used for raising the leakage preventing walls 31, 31 does not act on the rear central region 20D and its surroundings, the concavely curve surface of the rear portion of the sanitary napkin 1 will not be affected by the elastic shrinkage force of the elastically extensible members 32.

With respect to the widened portion 20B defined between the inflected portions 11B, 11B, furthermore, a compressive force from the front outer compressed grooves 15, 15 and the front side regions 21, 21 toward the longitudinal centerline Oy—Oy is applied to the front central region 20A that is positioned forward of the inflected portions 11B, 11B, while a compressive force from the rear outer compressed grooves 16, 16 and the rear side regions 24, 24 toward the longitudinal centerline Oy—Oy is applied to the rear central region 20D that is positioned rearward of the inflected portions 11B, 11B. Still furthermore, a compressive force is applied forward to the widened portion 20B from the front ends 16D, 16D of the rear outer compressed grooves 16, 16 due to a deforming force caused when the sanitary napkin 1 is concavely deformed according to the contour of the wearer's body and due to the elastic shrinkage force of the elastically extensible members 32 for raising the leakage preventing walls 31.

As a result, the widened portion 20B defined between the inflected portions 11B, 11B receives a compressive force from four directions, i.e., both in front and in the rear at both right and left sides thereof, so that the widened portion 20B is deformed to bulge toward the wearer's skin as if it were picked up from four directions. Accordingly, the widened portion 20B comes into close contact with the perineum (O) shown in FIG. 8.

Figure 6:
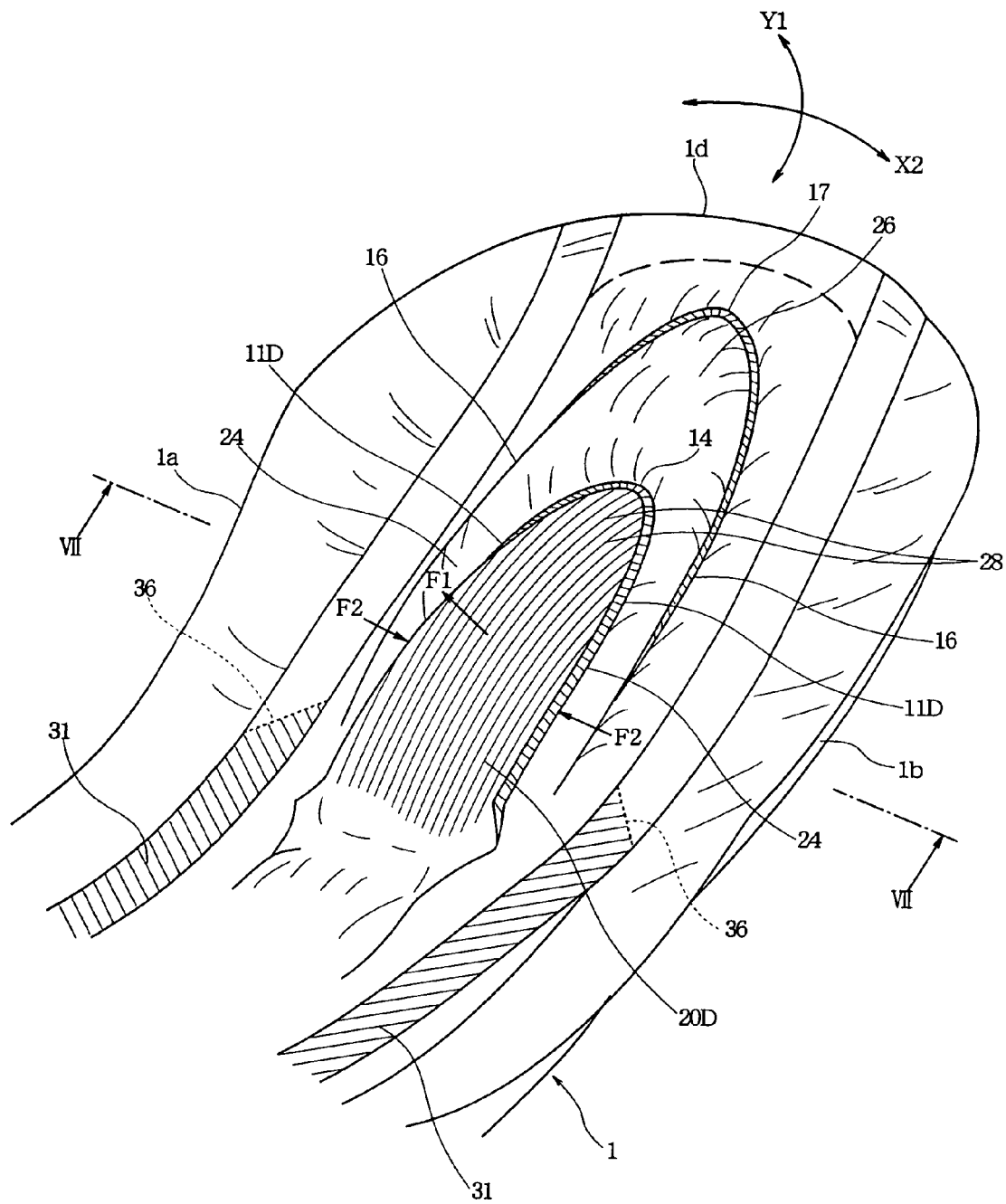
FIG. 6 is a perspective view showing how a rear portion of the sanitary napkin will be deformed.

In the sanitary napkin 1 in which the front central region 20A can be deformed to bulge and come into close contact with the vaginal opening (N), as set forth above, the widened portion 20B defined between the inflected portions 11B, 11B easily comes into close contact with the perineum (O), the rear central region 20D easily enters the cleft (Q) of the buttocks, and the rear portion easily conforms to the curved surface of the buttocks. Therefore, most of menstrual blood discharged from the vaginal opening (N) can be passed through the liquid passage holes 25 and absorbed by the liquid absorbent layer 4 in the front central region 20A, wherein menstrual blood trying to move rearward can be certainly collected by the rear central region 20D in close contact with the area from the perineum (O) to the cleft (Q) of the buttocks. Moreover, since the rear portion of the sanitary napkin 1 deformed into the three-dimensionally concavely curved state shown in FIG. 6 is able to come into close contact with the buttocks, outward leakage of menstrual blood from the rear portion can be effectively prevented during sleep and so on.

Figure 9:
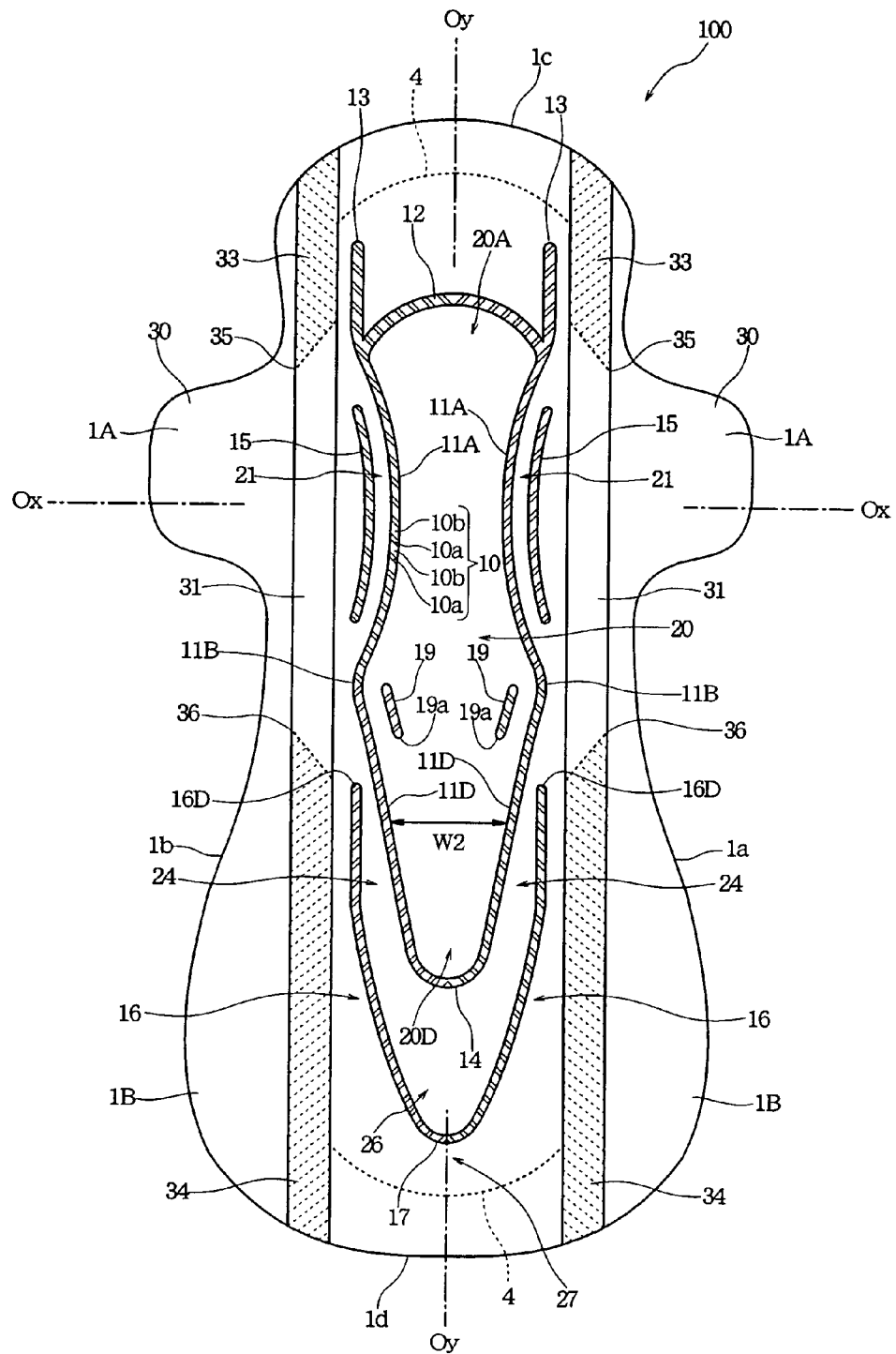
FIG. 9 is a top plan view showing a sanitary napkin according to another embodiment of the present invention.
Figure 10:
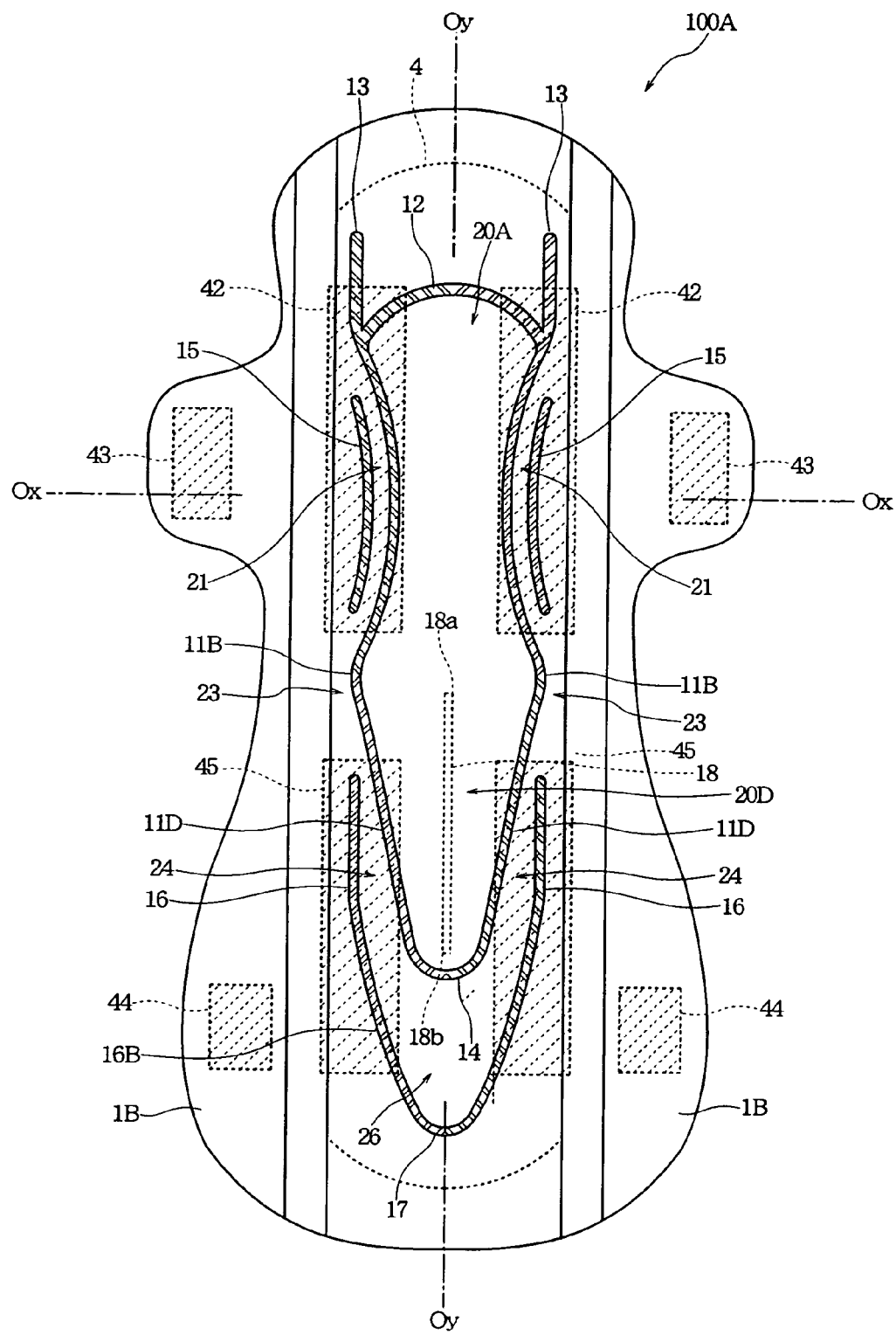
FIG. 10 is a top plan view showing a sanitary napkin according to still another embodiment of the present invention.
Figure 11:
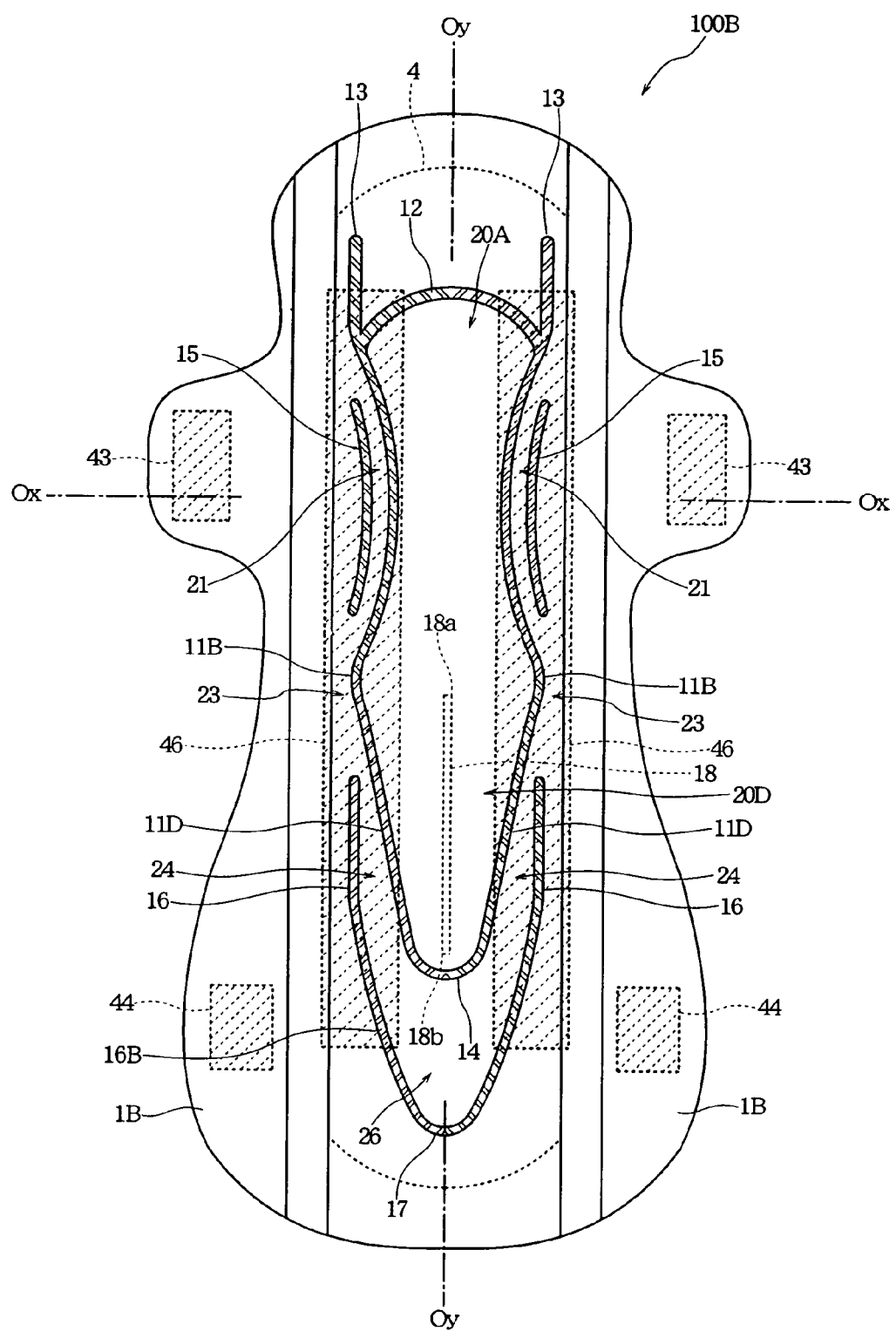
FIG. 11 is a top plan view showing a sanitary napkin according to still another embodiment of the present invention.

FIGS. 9 to 11 are top plan views showing sanitary napkins according to other embodiments of the present invention.

In the embodiments shown in FIGS. 9 to 11, only the portions different from those of the first embodiment shown in FIG. 1 and so forth will be described hereinbelow; the detailed description of the portions similar to those of the first embodiment of FIG. 1 will be omitted by designating them by the common reference numerals.

FIG. 9 shows a sanitary napkin 100, wherein short compressed grooves 19, 19 are disposed between the rear inner compressed grooves 11D, 11D in the rear central region 20D. The short compressed grooves 19, 19 are formed in the same manner as the compressed grooves 11–17. In the short compressed grooves 19, 19, therefore, the skin surface is recessed toward the garment surface with the liquid absorbent layer 4 compressed together with the topsheet 3. The short compressed grooves 19, 19 are relatively short and inwardly spaced an almost equal distance apart from the rear inner compressed grooves 11D, 11D.

When the portion of the rear central region 20D having the backside compressed portion 18 is raised up toward the wearer's body by the hanging-up force of the undergarment, the short compressed grooves 19, 19, particularly, rear ends 19a, 19a of the short compressed grooves 19, 19 function as starting points for folding, so that the region of the rear central region 20D positioned between the rear ends 19a, 19a and the rear connecting compressed groove 14 can be easily deformed to bulge toward the wearer's body, as shown in FIG. 7.

FIG. 10 shows a sanitary napkin 100A. In the rear portion of the sanitary napkin 100A, pressure-sensitive adhesive layers 45, 45 are provided on the exterior surface of the backsheet 2. The pressure-sensitive adhesive layers 45, 45 are disposed symmetrically about the longitudinal centerline Oy—Oy. The pressure-sensitive adhesive layers 45, 45 are similar in shape to but separate from the pressure-sensitive adhesive layer 42, 42 provided in the front portion of the sanitary napkin 100A.

The pressure-sensitive adhesive layers 45, 45 are formed to cover the rear inner compressed grooves 11D, the rear side regions 24 and the rear outer compressed grooves 16. However, no pressure-sensitive adhesive layers are provided on the backsheet 2 at portions laterally outside the inflected portions 11B, 11B.

In the front portion of the sanitary napkin 100A, since the front inner compressed grooves 11A, the front side regions 21 and the front outer compressed grooves 15 are firmly fixed to the undergarment through the pressure-sensitive adhesive layers 42, 42, the front central region 20A can be strongly compressed from both sides thereof by deformation of the undergarment during wear, thereby bulging toward the wearer's skin. In the rear portion, on the other hand, since the rear inner compressed grooves 11D, the rear side regions 24 and the rear outer compressed grooves 16 are firmly fixed to the inner side of the undergarment through the pressure-sensitive adhesive layers 45, 45, the rear central region 20D can be certainly compressed from both sides thereof by deformation of the undergarment during wear, so that the rear central region 20D can be deformed to bulge toward the wearer's body.

Furthermore, since the pressure-sensitive adhesive layers 42, 42 in the front portion and the pressure-sensitive adhesive layers 45, 45 in the rear portion are independent from each other, the front central region 20A and the rear central region 20D can move independently from each other so as to follow the movement of the undergarment.

FIG. 11 shows a sanitary napkin 100B, wherein pressure-sensitive adhesive layers 46, 46 are disposed symmetrically about the longitudinal centerline Oy—Oy. The individual pressure-sensitive adhesive layers 46, 46 are in the shape of an elongated strip formed by integrating the adjacent pressure-sensitive adhesive layers 42 and 45 together in the longitudinal direction. Also in the sanitary napkin 100B, right and left side portions of the front central region 20A and right and left side portions of the rear central region 20D are firmly fixed to the undergarment, so that the front central region 20A and the rear central region 20D can be certainly deformed by a lateral compressive force to bulge toward the wearer's body.

According to the present invention, as has been described hereinabove, the rear central region between the compressed grooves can easily come into close contact with an area from the anus to the cleft of the buttocks, and the rear portion can be deformed to provide a three-dimensionally concavely curved surface that can closely conform to the contour of the buttocks. Therefore, rearward leakage of menstrual blood from the absorbent article can be effectively prevented.

Although the present invention has been illustrated and described with respect to exemplary embodiments thereof, it should be understood by those skilled in the art that the foregoing and various other changes, omission and additions may be made therein and thereto, without departing from the spirit and scope of the present invention. In the present invention, for instance, the presence of the rear inner compressed grooves 11D, 11D and the rear connecting compressed groove 14 enables easy deformation of regions outside them into a three-dimensionally concavely curved state. Therefore, the rear outer compressed grooves 16, 16 and the outer rear connecting compressed groove 17 are not necessarily required. Accordingly, the present invention should not be understood as limited to the specific embodiments set out above but to include all possible embodiments which can be embodied within a scope encompassed and equivalent thereof with respect to the feature set out in the appended claims.

What is claimed is:

1. An elongated absorbent article comprising:
   a liquid-permeable topsheet appearing on a skin surface;
   a backsheet appearing on a garment surface; and
   a liquid absorbent layer disposed between the topsheet and the backsheet, the absorbent article having compressed groove where the skin surface is recessed toward the garment surface with the liquid absorbent layer compressed together with the topsheet,
   wherein the compressed groove includes: rear inner compressed grooves disposed in a rear half of the absorbent article and extending symmetrically about a longitudinal centerline of the absorbent article, defining therebetween a rear central region; and a rear connecting compressed groove connecting rear ends of the rear inner compressed grooves, defining a rear end of the rear central region,
   wherein the liquid absorbent layer is recessed in the rear central region from the side of the garment surface toward the skin surface to have a backside compressed portion extending along the longitudinal centerline, the backside compressed portion having a rear end positioned forward of the rear connecting compressed groove, and wherein rear outer compressed grooves are disposed laterally outside the rear inner compressed grooves to extend longitudinally of the absorbent article, and wherein density of the liquid absorbent layer is higher in regions positioned between the rear inner compressed grooves and the rear outer compressed grooves than in the rear central region.

2. An elongated absorbent article as set forth in claim 1, wherein the rear inner compressed grooves are formed to gradually decrease a separation distance therebetween rearwardly of the absorbent article.

3. An elongated absorbent article as set forth in claim 1, wherein the rear outer compressed grooves are connected with each other at a position spaced rearwardly apart from the rear connected compressed groove.

4. An elongated absorbent article as set forth in claim 1, wherein the compressed groove further includes: front inner compressed grooves extending forwardly from the rear inner compressed grooves without interruption; and front outer compressed grooves disposed laterally outside the front inner compressed grooves to extend longitudinally of the absorbent article, wherein inflected portions are provided at boundaries between the rear inner compressed grooves and the front inner compressed grooves to increase a separation distance between laterally opposed compressed grooves, the rear outer compressed grooves being spaced apart from the front outer compressed grooves in portions laterally outside the inflected portions.

5. An elongated absorbent article as set forth in claim 1, wherein elastically extensible members for exerting an elastic shrinkage force on the skin surface in the longitudinal direction are disposed so that rear action ends of the elastically extensible members are positioned forward of or in the vicinities of front ends of the rear outer compressed grooves.

6. An elongated absorbent article as set forth in claim 1, wherein the backsheet is bonded to the backside compressed portion of the liquid absorbent layer so that the backsheet fits in the recess of the backside compressed portion.

7. An elongated absorbent article as set forth in claim 1, wherein a pressure-sensitive adhesive layer is disposed on an exterior surface of the backsheet in a region elongated longitudinally of the absorbent article to cover the backside compressed portion.

8. An elongated absorbent article comprising:

a liquid-permeable topsheet appearing on a skin surface;

a backsheet appearing on a garment surface; and a liquid absorbent layer disposed between the topsheet and the backsheet, the absorbent article having compressed groove where the skin surface is recessed toward the garment surface with the liquid absorbent layer compressed together with the topsheet, wherein the compressed groove includes: rear inner compressed grooves disposed in a rear half of the absorbent article and extending symmetrically about a longitudinal centerline of the absorbent article, defining therebetween a rear central region; and a rear connecting compressed groove connecting rear ends of the rear inner compressed grooves, defining a rear end of the rear central region, wherein the liquid absorbent layer is recessed in the rear central region from the side of the garment surface toward the skin surface to have a backside compressed portion extending along the longitudinal centerline, the backside compressed portion having a rear end positioned forward of the rear connecting compressed groove, wherein the outer compressed grooves are disposed laterally outside the rear inner compressed grooves to extend longitudinally of the absorbent article, wherein the compressed groove further includes: front inner compressed grooves extending forwardly from the rear inner compressed grooves without interruption; and front outer compressed grooves disposed laterally outside the front inner compressed grooves to extend longitudinally of the absorbent article, and wherein inflected portions are provided at boundaries between the rear inner compressed grooves and the front inner compressed grooves to increase a separation distance between laterally opposed compressed grooves, the rear outer compressed grooves being spaced apart from the front outer compressed grooves in portions laterally outside the inflected portions.

9. An elongated absorbent article as set forth in claim 8, wherein the rear inner compressed grooves are formed to gradually decrease a separation distance therebetween rearwardly of the absorbent article.

10. An elongated absorbent article as set forth in claim 8, wherein the rear outer compressed grooves are connected with each other at a position spaced forwardly apart from the rear connecting compressed groove.

11. An elongated absorbent article as set forth in claim 8, wherein elastically extensible members for exerting an elastic shrinkage force on the skin surface in the longitudinal direction are disposed so that rear action ends of the elastically extensible members are positioned forward of or in the vicinities of front ends of the rear outer compressed grooves.

12. An elongated absorbent article as set forth in claim 8, wherein the backsheet is bonded to the backside compressed portion of the liquid absorbent layer so that the backsheet fits in the recess of the backside compressed portion.

13. An elongated absorbent article as set forth in claim 8, wherein a pressure-sensitive adhesive layer is disposed on an exterior surface of the backsheet in a region elongated longitudinally of the absorbent article to cover the backside compressed portion.

14. An elongated absorbent article comprising:

a liquid-permeable topsheet appearing on a skin surface;

a backsheet appearing on a garment surface; and liquid absorbent layer disposed between the topsheet and the backsheet, the absorbent article having compressed groove where the skin surface is recessed toward the garment surface with the liquid absorbent layer compressed together with the topsheet, wherein the compressed groove includes: rear inner compressed groove disposed in a rear half of the absorbent article and extending symmetrically about a longitudinal centerline of the absorbent article, defining therebetween a rear central region; and a rear connecting compressed groove connecting rear ends of the rear inner compressed grooves, defining a rear end of the rear central region, wherein rear outer compressed grooves are disposed laterally outside the rear inner compressed grooves to extend longitudinally of the absorbent article, wherein the liquid absorbent layer is recessed in the rear central region from the side of the garment surface toward the skin surface to have a backside compressed portion extending along the longitudinal centerline, the backside compressed portion having a rear end positioned forward of the rear connecting compressed groove, and wherein elastically extensible member for exerting an elastic shrinkage force on the skin surface in the longitudinal direction are disposed so that rear action ends at the elastically extensible members are positioned forward of or in the vicinities of front ends of the rear outer compressed grooves.

15. An elongated absorbent article as set forth in claim 14, wherein the rear inner compressed grooves art formed to gradually decrease a separation distance therebetween rearwardly of the absorbent article.

16. An elongated absorbent article as set forth in claim 14, wherein the rear outer compressed grooves are connected with each other at a position spaced rearwardly apart from the rear connecting compressed groove.

17. An elongated absorbent article as set forth in claim 14, wherein the backsheet is bonded to the backside compressed portion of the liquid absorbent layer so that the backsheet fits in the recess of the backside compressed portion.

18. An elongated absorbent article as set forth in claim 14, wherein a pressure-sensitive layer is disposed on an exterior surface of the backsheet in a region elongated longitudinally of the absorbent article to cover the backside compressed portion.

* * * * *